United States Patent
Farina et al.

(10) Patent No.: US 8,222,241 B2
(45) Date of Patent: Jul. 17, 2012

(54) USE OF DIMIRACETAM IN THE TREATMENT OF CHRONIC PAIN

(75) Inventors: Carlo Farina, Milan (IT); Carla Ghelardini, Pistoia (IT); Paola Petrillo, Milan (IT)

(73) Assignee: Neurotune AG, Schlieren (CH)

( * ) Notice: Subject to any disclaimer, the term of this patent is extended or adjusted under 35 U.S.C. 154(b) by 0 days.

(21) Appl. No.: 13/166,088

(22) Filed: Jun. 22, 2011

(65) Prior Publication Data

US 2011/0251250 A1    Oct. 13, 2011

Related U.S. Application Data

(62) Division of application No. 12/450,944, filed as application No. PCT/EP2008/054553 on Apr. 15, 2008.

(30) Foreign Application Priority Data

Apr. 16, 2007   (IT) .............................. MI2007A0770

(51) Int. Cl.
*A61K 31/44*   (2006.01)
*A61K 31/40*   (2006.01)
*A61P 23/00*   (2006.01)

(52) U.S. Cl. ........................................................ 514/183
(58) Field of Classification Search ........................ None
See application file for complete search history.

(56) References Cited

FOREIGN PATENT DOCUMENTS
WO   WO 2004/085438   * 10/2004

* cited by examiner

*Primary Examiner* — Brandon Fetterolf
*Assistant Examiner* — Anna Pagonakis
(74) *Attorney, Agent, or Firm* — Abelman, Frayne & Schwab

(57) ABSTRACT

The use of dimiracetam in the treatment of chronic pain is disclosed. At doses higher than those previously disclosed in relation with its cognition enhancing activity (i.e. amelioration of learning and memory), dimiracetam was able to completely revert hyperalgesia or allodynia associated with several animal models of chronic pain. Dimiracetam showed high activity in iatrogenic neuropathies associated with antiviral and chemotherapeutic drug treatments and in painful conditions caused by osteoarthritis. In addition, dimiracetam was devoid of toxicity even at doses 10-fold higher than the highest therapeutic dose. The possibility of treating such debilitating pathologies with a highly effective and essentially non-toxic compound is therefore disclosed.

11 Claims, 7 Drawing Sheets

USE OF DIMIRACETAM IN THE TREATMENT OF CHRONIC PAIN

CROSS-REFERENCE TO RELATED APPLICATIONS

This application is a divisional of U.S. application Ser. No. 12/450,944, filed Oct. 16, 2009, which is a National Phase of PCT/EP2008/054553, filed Apr. 15, 2008, which claims priority from Italian Application MI2007A000770, filed Apr. 16, 2007, all of which are incorporated herein by reference.

FIELD OF THE INVENTION

The present invention relates to the field of pharmacological treatment of chronic pain.

BACKGROUND OF THE INVENTION

Differently from acute pain, which exerts an important physiological action alerting the organism towards an incoming danger or damage, chronic pain is not involved in any protective action.

Chronic pain may be divided in two main categories: chronic inflammatory pain and neuropathic pain. The latter is due to a direct lesion on the nervous pathways by the noxa, which can be infectious, metabolic, vascular or other. In chronic inflammatory pain the lesioned tissues release algogenic factors which in turn damage nerve terminals creating a vicious mechanism which maintains and potentiates the perception of pain (hyperalgesia) or transforms into pain other types of perception (allodynia).

Chronic pain, of both neuropathic and inflammatory origin, is an important epidemiologic aspect of a high unmet medical need condition; in fact this is a therapeutic area presently characterized by modestly effective and poorly tolerated treatments.

An increasing number of patients suffer from iatrogenic neuropathic pain, induced by anti-tumor therapies used in modern oncology. In particular taxol derived drugs, cisplatin and vincristine are among the drugs which more often induce painful neuropathies. Currently no effective and/or well tolerated treatments exist for this kind of pain. In fact classical antiepileptic or antidepressive agents successfully used in other forms of neuropathic pain, such as lamotrigine (Renno S. I. 2006, *J. Clin. Oncol. ASCO Annual Meeting Proceeding Part I* vol. 24, No 18S:8530), gabapentin (Wong G. Y. 2005, *J. Clin. Oncol. ASCO Annual Meeting Proceeding Part I* vol. 23, No 16S:8001) or nortriptyline (Hammack J. E. 2002, *Pain* 98:195-203) are absolutely unsatisfactory on the basis of their therapeutic index.

Nucleoside analogue reverse transcriptase inhibitors (ddC, d4T, AZT) are commonly used as antiviral drugs in the treatment of AIDS. These drugs often cause the insurgence of peripheral neuropathies with different degrees of severity after prolonged treatment. As in the case of chemotherapeutic agents, these symptoms may be so strong to induce shortening or suspension of these life-saving therapies. The patterns of these neuropathies are clearly different from those induced by the progression of AIDS; they are in fact characterized by the sudden onset of very intense burning discomfort in both hands and feet at about the tenth week of treatment. HIV-induced neuropathies, on the contrary, have a very slow progression (Dubinsky R. M. 1989, *Muscle Nerve* 12:856-860). As for chemotherapy-induced neuropathies, it is difficult to treat this kind of pain.

The tricyclic antidepressant amitryptiline and the sodium channel blocker mexiletine, effective on various forms of painful peripheral neuropathies, did not show any significant effect on this kind of neuropathic pain (Kieburtz K. 1998 *Neurology* 51:1682-1688). Gabapentin showed some efficacy, although patients with severe syndromes rarely reach satisfactory results and the additional administration of narcotics is required (McArthur J. C. 2001, *The Hopkins HIV report*. http://www.hopkins-aids.edu/publications/report/may01_2.html).

Other forms of neuropathic pain may be caused by viral infections. Postherpetic neuralgia, for instance, is caused by the reactivation, long after the infection, of the varicella-zoster virus. This kind of neuropathy is characterized by the development of strong mechanical allodynia, frequent loss of sensitivity towards thermal stimuli and spontaneous intermitting pain. Pain intensity compromises the quality of life of patients suffering from this condition.

Of high epidemiological relevance is the pain referred to as cephalalgia. This is localized to the head, face and neck. When cephalea occurs in a paroxystic way, with recurrent episodes lasting from hours to days and is associated to general sickness, it is called migraine. Several forms of migraine are recognized such as common, classical, hemiplegic, vertebro-basilar, etc.

The current treatment for migraine entails the use of different kinds of analgesic agents, from non-steroidal anti-inflammatory drugs (NSAIDs) to opioids, antihistaminic drugs and ergotamine derivatives. In the last decade triptan 5HT2 antagonists have been used; they are often able to block an attack at its insurgence, if promptly administered. All these treatments show serious limits in terms of both efficacy and tolerability. In the most severe cases, in which painful attacks recur many times a week, a pre-emptive therapy with antiepileptic, beta blocker and antidepressant drugs is performed. The maximum result which can be achieved with these pre-emptive therapies is 50% reduction in the frequency and intensity of the painful attacks, but not their definitive remission.

Inflammatory pain is another form of chronic pain. It is caused by the release of mediators which either directly activate the nociceptors localized on primary afferents, or lower their activation threshold, thus increasing their sensitivity to either painful or non-painful stimuli of different nature. Excited primary afferents may in turn release neurotransmitters which can stimulate immune cells recruited by the inflammatory process causing the release of additional inflammatory mediators.

This phenomenon, defined 'neurogenic inflammation', leads to an autoamplification of the symptomatology of the patient. Osteoarthritis is a particularly severe and painful form of this kind of pathology. Osteoarthritis is a form of degenerative arthritis causing the breakdown and eventual loss of the cartilage of one or more joints. The most common symptom related to this pathology is pain in the affected joint after repetitive use or after prolonged periods of inactivity (night and rest pain). Even if a certain correlation between pain and the extension of the damage at the joint has been demonstrated, the precise etiology of this kind of pain is still obscure; in fact, patients with relatively small damages at the joints suffer from very intense pain and vice versa; this finding suggests that it is not a merely inflammatory pain, but that a neuropathic component is present as well. Recommended treatments include NSAIDs, steroids and opioids, but the use of these drugs is associated with the insurgence of severe side-effects; in addition, they do not show full efficacy in many instances (Altman R. D. 2000 *Arthritis Rheum.* 43:1905-1915).

The fibromyalgia syndrome is the most frequent cause of chronic, widespread pain, associated with auxiliary symptoms, such as sleep disturbances and chronic fatigue (Rao S. G. 2007, *Psychopharmacol. Bull.* 40:24-67). Nearly 2% of the general population in the United States suffers from fibromyalgia, with females of middle age being at increased risk. Patients with fibromyalgia display quantitative abnormalities in pain perception under experimental conditions, in the form of both allodynia and hyperalgesia: these data are suggestive of a state of sensitized pain perception.

Recently, pregabalin and duloxetine showed some efficacy in clinical trials for the treatment of the muscle pain in fibromyalgia (Crofford L. J. 2005, *Arthritis Rheum.* 52:1264-1273; Maizels M. 2005, *Am. Fam. Physician* 71:483-490). Nonetheless, at present, the medical treatment for pain relief in fibromyalgia is unsatisfactory (Offenbaecher M. 2005, *CNS Spectr.* 10:285-297) and fibromyalgia represents a high unmet medical need.

Dimiracetam (2,5-dioxohexahydro-1H-pyrrolo[1,2-a]imidazole) is a bicyclic pyrrolidinonic derivative of formula (I)

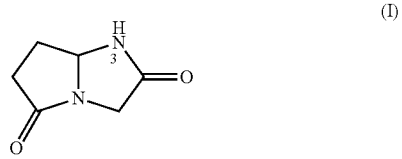

(I)

Patent application EP-A-335483 claims its pharmaceutical use as a nootropic agent, i.e. able to improve learning and memory in humans and animals. Dose-response data show that the nootropic activity of dimiracetam tends to lower for oral doses greater than 10 mg/kg (*J. Med. Chem.*, 1993, 36:4214-4220). Patent application WO-A-93/09120 claims a process for the preparation of dimiracetam and of its enantiomers.

WO-A-2004/085438 claims a set of derivatives of 2,5-dioxohexahydro-1H-pyrrolo[1,2-a]imidazole; a typical feature of these compounds is the presence, in position 3 of the imidazole ring, of an aromatic carbocyclic or heterocyclic ring; these compounds, notwithstanding their utility in the treatment of painful conditions, show a therapeutic index which is not fully satisfactory.

In view of the above mentioned background the need is felt for new drugs endowed with high antihyperalgesic and anti-allodynic activity towards chronic pain, and characterized by a high therapeutic index. The need is also felt for the treatment of specific forms of neuropathic pain which are not well treated with traditional antihyperalgesic agents.

SUMMARY OF THE INVENTION

The present inventors have studied the behaviour of dimiracetam at different doses with respect to those previously described for this compound, considering also possible variations of toxicity associated to the new doses. During these studies a new pharmacological window has been found, within which dimiracetam exerts a strong regression effect on chronic painful phenomena of neuropathic or inflammatory origin, without showing any toxic effect. The possibility to treat these debilitating pathologies with an effective and essentially atoxic compound is therefore disclosed.

DETAILED DESCRIPTION OF THE INVENTION

Figure 1:
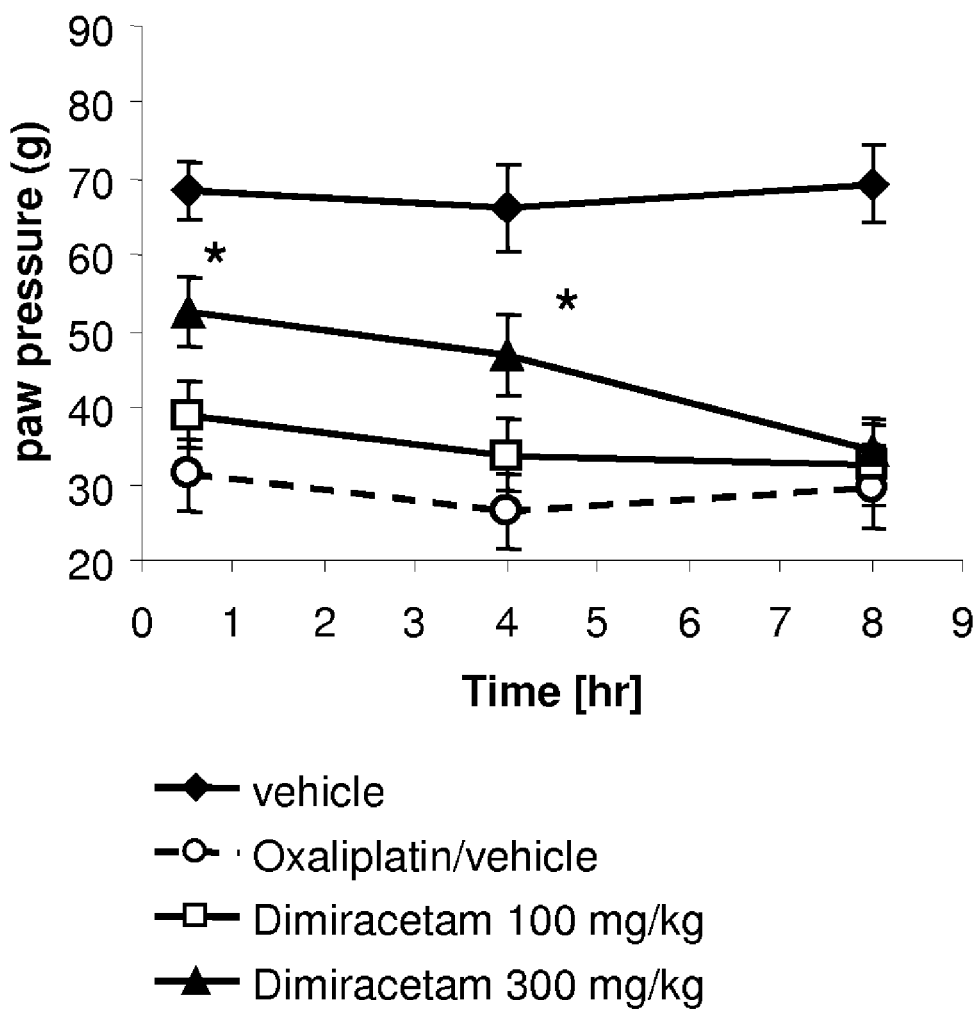
FIG. 1: Oxaliplatin-induced neuropathy
*$p<0.01$ vs oxaliplatin/vehicle treated group. Each value represents the mean±S.E.M. of 8-11 rats. Compounds were administered starting three days before oxaliplatin treatment.

A first object of the present invention is the use of dimiracetam, or a pharmaceutically acceptable solvate thereof, in the manufacture of a medicament useful for treating and/or preventing chronic pain. The invention is also directed to dimiracetam, or a pharmaceutically acceptable solvate thereof, for use in the treatment and/or prevention of chronic pain.

A further object of the present invention is a method for treating and/or preventing chronic pain, consisting in the administration of a pharmaceutically effective dose of dimiracetam to a patient in need thereof.

Dimiracetam is a chiral compound. For the scope of the present invention, the term "dimiracetam" identifies the isolated (R) or (S) enantiomers of dimiracetam, or mixtures thereof in which the two enantiomers are present in equal or different amounts. It is therefore intended that the use, method and pharmaceutical compositions which are the object of the present invention are extended to those mixtures or the single enantiomers of dimiracetam.

According to the present invention, dimiracetam may be administered as such or in association with any other active principle useful for the treatment or prevention of chronic pain or diseases causing it.

It is also part of the invention the administration of dimiracetam in association with active principles which present as side effect the insurgence of chronic pain, in particular anti-tumor and antiviral drugs; non-limiting examples of such drugs are taxol, vincristine, cisplatin, oxaliplatin, nucleoside reverse transcriptase inhibitor antivirals (ddC, d4T, AZT), many of which are gold standard antiviral drugs in HIV infection therapy.

By means of the claimed use and method it is possible to treat effectively and with high safety all kinds of chronic pain, either neuropathic or inflammatory in origin. Preferred examples of chronic pain treated according to the present invention are the following:

1. pain induced by chemotherapeutic agents or other antiblastic therapy (e.g. radiotherapy); among the chemotherapeutic agents responsible for neuropathies, taxol, vincristine, cisplatin, oxaliplatin are mentioned;
2. pain induced by antiviral agents such as nucleoside reverse transcriptase inhibitors (ddC, d4T, AZT);
3. complex regional pain syndrome, phantom limb, thalamic syndromes, spinal syndromes;
4. pain induced by osteoarthritis, rheumatoid arthritis, autoimmune osteoarthrosis forms;
5. pain induced by cephalea (cephalea in general and hemicranic forms; cephalea due to vascular, infective, autoimmune, dysmetabolic and tumoral causes, cephalea from endocranial hypertension, cephalea from pseudotumor cerebri, classic hemicrania with and without aura, hemiplegic hemicrania and with other motor complications, childhood and juvenile hemicrania, Bickerstaff's syndrome, etc.).
6. pain induced by fibromyalgia Of outstanding efficacy, and therefore preferred in the scope of the invention, is the treatment of pain induced by antiviral agents, osteoarthritis, rheumatoid arthritis and autoimmune osteoarthritis.

In the scope of the invention, in the present treatment the antihyperalgesic effect of dimiracetam is exerted in a range of oral dosages between 10 and 300 mg/kg, preferably between 100 and 300 mg/kg. The antihyperalgesic effect may be achieved also by routes of administration different from the oral route, i.e. intramuscular or intravenous: in these cases dimiracetam is administered in amounts which allow to obtain haematic levels comparable to those obtained after oral administration of 10-300 mg/kg. Reference values useful for intramuscular administrations range from about 5 to about 150 mg/kg; reference values useful for intravenous administrations range from about 2 to about 60 mg/kg.

The invention encompasses therefore pharmaceutical compositions of dimiracetam useful for the above mentioned treatments. These compositions contain an amount of this active principle which is greater than that previously proposed for the nootropic activity.

The amounts of the active principle, expressed in mg/kg, are those cited above. These compositions have a dosage unit useful to administer the above mentioned dosages. Typically they contain from 500 to 15000 mg in case of oral compositions; from 250 to 7500 mg in case of intramuscular compositions; from 100 to 3000 mg in case of intravenous compositions.

Dimiracetam may be pharmaceutically formulated according to known methodologies. The various pharmaceutical compositions may be selected according to the needs of the treatment.

Such compositions can be prepared by mixing and can be suitably adapted for oral or parenteral administration, and as such, can be administered in the form of tablets, capsules, oral preparations, powders, granules, pellets, liquid solutions for injection or infusion, suspensions or suppositories.

Tablets and capsules for oral administration are usually supplied in dosage units and may contain conventional excipients such as binders, fillers, diluents, tabletting agents, lubricants, detergents, disintegrants, colorants, flavors and wetting agents. Tablets may be coated in accordance to methods well known in the art.

Suitable fillers include for example cellulose, mannitol, lactose and similar agents. Suitable disintegrants include starch, polyvinylpyrrolidone and starch derivatives such as sodium starch glycolate. Suitable lubricants include, for example, magnesium stearate. Suitable wetting agents include for example sodium lauryl sulfate.

These solid oral compositions can be prepared with conventional mixing, filling or tabletting methods. The mixing operations can be repeated to disperse the active agent in compositions containing large quantities of fillers. These operations are conventional.

The oral liquid compositions can be provided in the form of, for example, aqueous or oily suspensions, solutions, emulsions, syrups or elixirs or in the form of a dry product to be reconstituted with water or with a suitable liquid carrier at the time of use. The liquid compositions can contain conventional additives such as suspending agents, for example sorbitol, syrup, methylcellulose, gelatin, hydroxyethylcellulose, carboxymethylcellulose, aluminium stearate gel or hydrogenated edible fats, emulsifying agents, for example lecithin, sorbitan monooleate, or acacia; non aqueous carriers (which can include edible oil) for example almond oil, fractionated coconut oil, oily esters such as glycerin esters, propylene glycol or ethyl alcohol; preservatives, for example methyl or propyl p-hydroxybenzoate or sorbic acid and if desired, conventional flavours or colorants. Oral formulations also include conventional sustained release formulations, such as tablets or granules with enteric coating.

For parenteral administration, fluid dosage units can be prepared containing the active compounds and a sterile carrier. The active compounds, depending on the carrier and concentration, can be suspended or dissolved. The parenteral solutions are normally prepared by dissolving the compound in a carrier and sterilizing by filtration, before filling suitable vials or ampoules and sealing. Adjuvants such as local anaesthetics, preservatives and buffering agents can be advantageously dissolved in the carrier. In order to increase stability, the composition can be frozen after filling the vial and the water removed under vacuum. The parenteral suspensions are prepared essentially in the same way, with the difference that the active compounds can be suspended rather than dissolved in the carrier, and can be sterilized by exposure to ethylene oxide prior to being suspended in the sterile carrier. A surfactant or humectant can be advantageously included to facilitate uniform distribution of the compound of the invention.

A further method of administration for the compound of the invention refers to a topic treatment. Topic formulations may contain for example ointments, creams, lotions, gels, solutions, pastes and/or may contain liposomes, micelles and/or microspheres.

A further method of administration for the compounds of the invention is transdermal delivery. Typical transdermal formulations include conventional aqueous and non-aqueous vectors, such as creams, oil, lotions or pastes or may be in the form of membranes or medicated patches.

As is the common practice, the compositions are normally accompanied by written or printed instructions, for use in the treatment concerned.

Examples of the present invention are provided in what follows, purely for illustrative and non-limiting purposes.

EXPERIMENTAL PART

1. Methods 1.1 Chemotherapy-Induced Peripheral Neuropathy (CIPN)

Peripheral neuropathy is induced by repeated administration of vincristine, taxol or oxaliplatin to adult male Sprague-Dawley rats (150-200 g, supplier Harlan).

The following protocols were used respectively:

Vincristine: the drug was injected by intravenous route at the dose of 150 µg/kg. The treatment was performed every 2 days, for 5 times, until a cumulative dose of 750 µg/kg was reached. Paw pressure test was performed 4 days after the last injection (Marchand F. et al. 2003, *Brain Res.* 980:117-120).

Taxol: taxol neuropathy was induced by intraperitoneal administration of 0.5 mg/kg once a day, on days 1, 3, 5 and 8. Cumulative taxol dose was 2 mg/kg. The pharmacological test was performed 14-18 days after the last taxol injection (Polomano R. C. et al. 2001, *Pain* 94:293-304).

Oxaliplatin: 2.4 mg/kg were injected by intraperitoneal route for 5 consecutive days followed by 2 days suspension (one cycle). A total of 3 cycles was performed, reaching a cumulative dose of 36 mg/kg (Cavaletti G. 2001, *Eur. J. Cancer* 37:2457-2463). The test was performed 48 h after the last oxaliplatin injection.

1.2 Antiviral-Induced Neuropathy

Adult male Sprague Dawley rats (150-200 g, supplier Harlan) were treated by intravenous route with a single administration of 25 mg/kg of nucleoside reverse transcriptase inhibitors ddC (2',3'-dideoxycytidine) or d4T (2',3'-didehydro-3'-deoxythymidine). Administration of these anti-HIV drugs induced a marked allodynic response to a mechanical stimulus (Joseph E. K. 2004, *Pain* 107:147-158). The maximum reduction of the paw pressure threshold is developed between day 5 and day 10 after injection. The test was performed on day 10.

1.3 Cephalea

Experimental models in rats demonstrated that meninges and cerebral blood vessels are pain-sensitive structures and are heavily innervated by the trigeminal nerve. Activation of trigeminal fibers causes a neurogenic inflammatory response of meningeal tissues, that has been proposed as an essential mechanism for migraine pain and other headaches. (Bolay H. 2002, *Nature Medicine* 8:136-142). On these basis, animal models of blood vessel neuro-inflammation following electrical trigeminal stimulation were commonly utilized to discover potential effective drugs. Adult male Sprague-Dawley rats (150-200 g weight, Harlan) were anaesthetized with pentobarbital Sodium® (60 mg/kg i.p.), and placed in a stereotaxic frame. An ipsilateral electrode was then inserted and trigeminal nucleus was stimulated to induce a meningeal neuroinflammation, which can be detected by the amount of extravasated Blue Evans dye or radiolabelled bovine serum albumine.

1.4 Arthritic Pain in Rats

Joint inflammation was induced by intra-articular injection of 0.1 ml of Freund's complete adjuvant (CFA) in anaesthetized rats (male adult Sprague Dawley rats, 150-200 g, supplier Harlan). Mechanical hyperalgesia was evaluated using the paw pressure test 14 days after CFA administration (Shan S 2006, *Pain* 129:64-75).

1.5 Osteoarthritis-Related Pain in Rats

Osteoarthritis was induced by a single administration of 2 mg (in a volume of 25 µl) of sodium 2-iodoacetate into the left knee joint of anaesthetized rats (male adult Sprague Dawley rats, 150-200 g, supplier Harlan) (Fernihough J. 2004, *Pain* 112:83-93). This treatment induces the progressive degeneration of the joint and the development of hyperalgesia, mimicking at the histological and behavioral levels what observed in humans. Pharmacological test was performed 7 days after treatment.

1.6a Evaluation of Mechanical Hyperalgesia: Paw Pressure Test

Mechanical hyperalgesia in rats (male adult Sprague Dawley rats, 150-200 g, supplier Harlan) was determined using the paw pressure test. The nociceptive threshold was determined with an analgesimeter (Ugo Basile, Italy), exerting a force that increases at constant rate (32 g/s) according to the method described by Leighton G. E. 1988, *Br. J. Pharmacol.* 93:553-560. The stimulus causing paw withdrawal was evaluated before and at different times after treatment. Results represent the mean of mechanical thresholds expressed as grams. To avoid any possible damage to the animal paw the maximum applied force was fixed at 240 g.

1.6b Evaluation of Mechanical Allodynia: Von Frey Test

Rats (male adult Sprague Dawley rats, 150-200 g, supplier Harlan) were placed in a chamber with a mesh metal floor covered by a plastic dome that enabled the animals to walk freely, but not to jump. The mechanical stimulus was delivered in the mid-plantar skin of left hind paw using an electronic von Frey apparatus. The cut-off was fixed at 50 g, while the increasing force rate (ramp duration) was settled at 20 sec.

1.7 Irwin Test in Rats

To verify if the administration of the compound may induce centrally mediated side effects, adult male Sprague Dawley rats (150-200 g, supplier Harlan) were treated with dimiracetam by subcutaneous and oral routes and monitored according to the "Irwin test" protocol (Irwin 1968, *Psychopharmacologia* 13:222-257), a systematic and quantitative procedure for assessing the behavioral and physiological modifications induced in animals by the drug treatment.

Rats were constantly monitored for 30 min after administration. Monitoring was iterated every morning at 9 a.m. for 4 days after administration.

1.8 Motor Coordination in Rats

The rotarod test allows the evaluation of the effects of a compound on motor coordination. Adult male Sprague Dawley rats (200-220 g, supplier Harlan, Milan) were placed on a plastic rod 6 cm in diameter and 35 cm in length, rotating at constant speed (16 rpm) at a height of 25 cm. The rod is divided in 4 equal sections, thus up to 4 animals may be tested simultaneously. The animals were required to walk against the motion of the rotating drum over 30 seconds. The time taken to fall off the rotarod was recorded as number of falls in 30 seconds, following the method of Vaught et al. 1985, *Neuropharmacology* 24:211-216. In each experiment motor coordination is measured before (pre-test) and after administration of the tested compound. Rats scoring less than 3 and more than 6 falls in the pretest are rejected.

1.9 Rotarod/Ataxia Test in Rats

The test was performed according to the method described by Veneroni et al 2003, *Pain* 102:17-25. Neurological deficits were evaluated by the inability of the rats to remain on the rotating rod (10 rpm) for the test period. The toxic dose was calculated as the dose causing 25% ($TD_{25}$) or 50% ($TD_{50}$) of the fallen rats (only for gabapentin, the toxic dose was $TD_{16}$=16% of fallen rats).

1.10 Hole Board in Mice

The hole board test allows to study the behavior of rodents when confronted with a new environment (Boissier J R 1964, *Therapie* 19:571-583). The test enables to evaluate the initial exploratory activity of the animal and its possible variations induced by drug administration.

The hole board test uses a 40 cm square plane with 16 flush-mounted cylindrical holes (diameter 3 cm) distributed 4 by 4 in an equidistant, grid-like manner. Mice (male Swiss Webster mice weighing 25-30 g, supplier Morini) are placed one by one in the center of the board and allowed to move freely, each for a period of 5 min. Two photoelectric beams, crossing the plane from mid-point to mid-point of opposite sides, and thus dividing the plane into four equal quadrants, automatically record the movements of the animals on the plane surface. Miniature photoelectric cells in each of the 16 holes record the exploration of the holes (head plunging activity) by the mice.

2. Results (Antihyperalgesic Activity)

2.1 Oxaliplatin-Induced Neuropathy in Rats

The effect of dimiracetam was evaluated in the oxaliplatin-induced neuropathy model after repeated administration with the paw pressure test. Results are reported in FIG. 1. Dimiracetam was administered at doses of 100 and 300 mg/kg p.o. once a day, starting three days before oxaliplatin treatment and during the treatment itself. At the dose of 300 mg/kg, dimiracetam significantly reduced mechanical hyperalgesia. The effect was statistically significant between 30 min and 4 h after administration.

2.2 Antiviral-Induced Neuropathy

Figure 2:
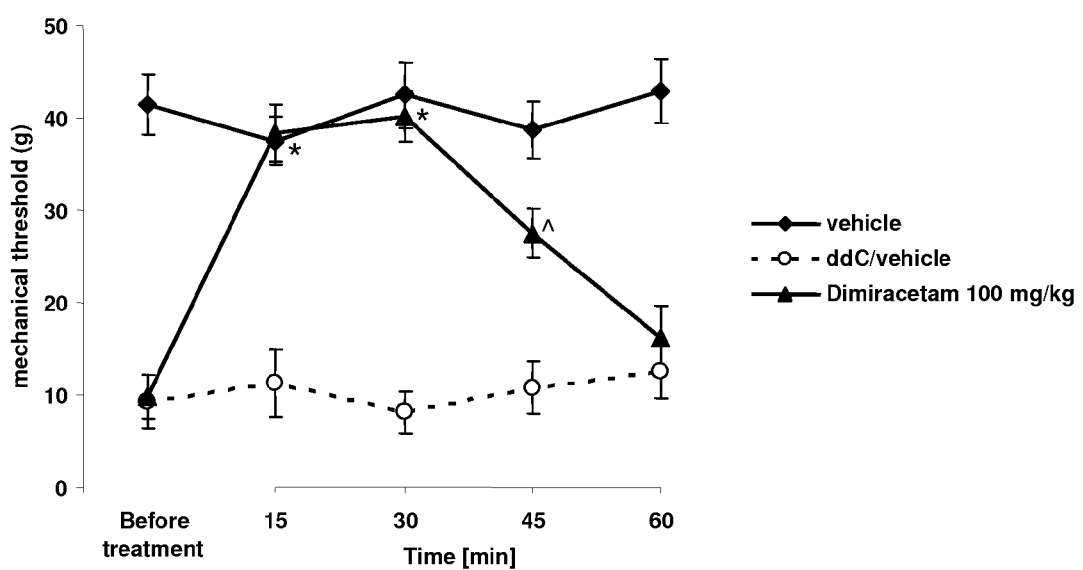
FIG. 2: ddC-induced neuropathy
*$p<0.01$, ^$p<0.05$ vs ddC/vehicle group. Each value represents the mean±S.E.M. of mechanical threshold expressed as grams, with a total of 10 rats per group.

Test results (von Frey test) are reported in FIG. 2. At the dose of 100 mg/kg, 15-30 min after administration, dimiracetam fully reverted ddC-induced allodynia, the mechanical threshold being at the same level in treated and control animals. The effect was still statistically significant 45 min after treatment.

Figure 3:
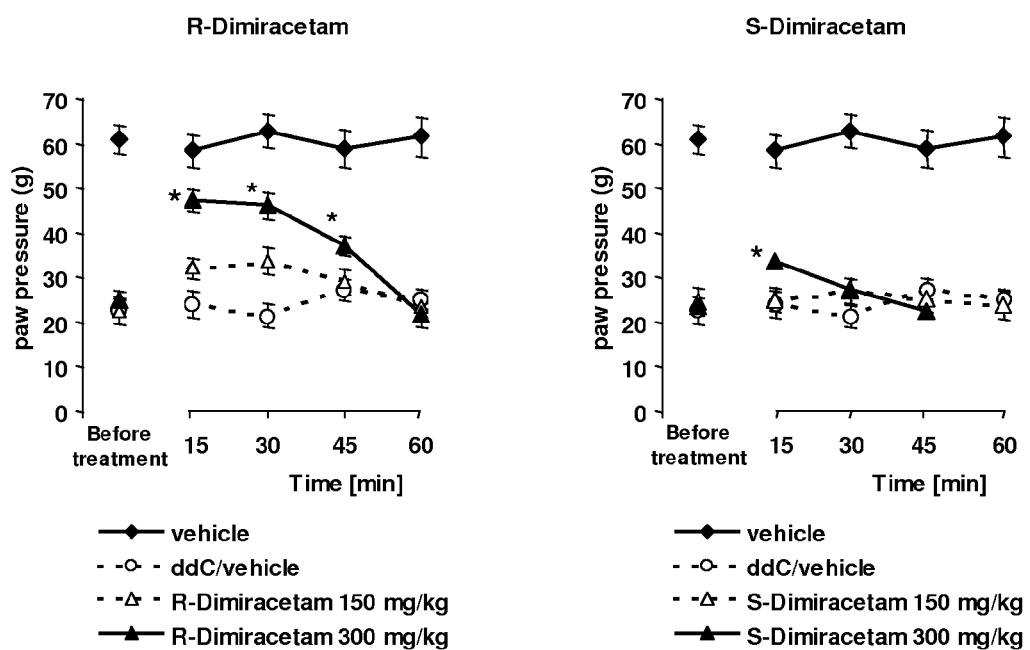
FIG. 3: ddC-induced neuropathy
*$p<0.01$ vs ddC/vehicle group. Each value (with the exception of the control group) represents the mean±S.E.M. of 18 rats in two experiments.

Dimiracetam is a racemic compound; the two corresponding enantiomers were synthesized and separately tested in the ddC-induced neuropathy model. The two compounds were administered orally at doses of 150 and 300 mg/kg and their antihyperalgesic activity was evaluated with the paw pressure test. Results are reported in FIG. 3. (R)-dimiracetam induced a significant reduction of the pain mechanical threshold at 300 mg/kg, 15-45 min after administration. The (S) enantiomer induced a significant effect at 300 mg/kg, 15 min after administration. These data demonstrate the efficacy also of the single enantiomers of dimiracetam.

2.3 Osteoarthritic Pain in Rats

Figure 4:
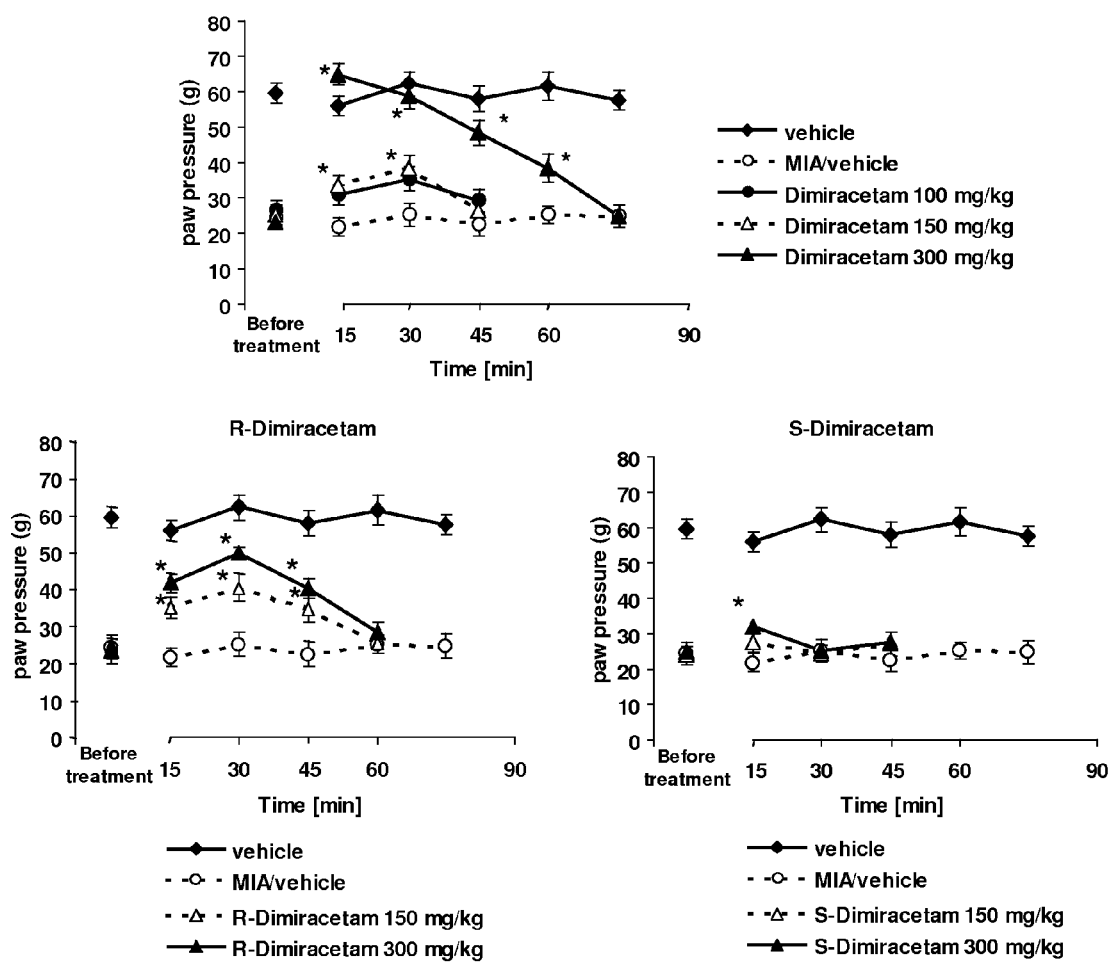
FIG. 4: MIA-induced osteoarthritic pain in rats
*$p<0.01$ vs MIA/vehicle group. Each value represents the mean±S.E.M. of 18 rats in two experiments.

The antihyperalgesic potential of dimiracetam was evaluated (paw pressure test) in the osteoarthritic pain model induced by the intra joint injection of sodium monoiodoacetate (MIA). Test results are reported in FIG. 4. Both dimiracetam and its (R) enantiomer at the dose of 150 mg/kg, 15-30 min after administration, showed a statistically significant effect in reverting MIA-induced hyperalgesia. At the dose of 300 mg/kg dimiracetam fully reverted MIA-induced hyperalgesia, the mechanical threshold being at the same level in treated and control animals between 15 and 45 min after administration; the effect was still statistically significant 60 min after administration. The effect of the (R) enantiomer was still statistically significant 45 min after treatment.

3. Results (Tolerability)

In order to verify if dimiracetam may induce unwanted side effects, the compound was tested in the rotarod model (motor coordination and ataxia) in rats and in the hole board model (spontaneous and exploratory activity) in mice.

3.1 Rotarod Test in Rats

Figure 5:
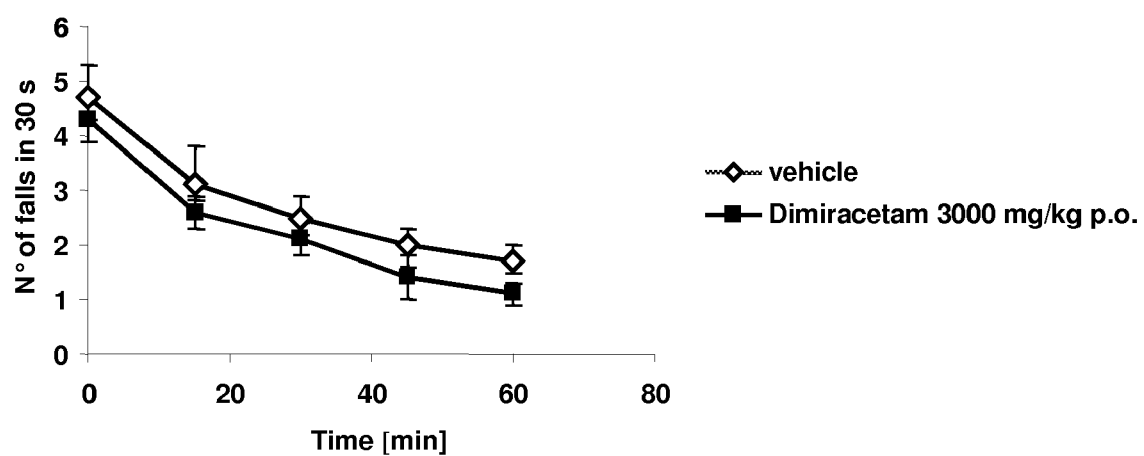
FIG. 5: Motor coordination in rats (rotarod)
Each value represents the mean±S.E.M. of the number of falls in 30 sec. of groups of 8 rats.

In acute toxicity experiments, dimiracetam, administered at 3000 mg/kg p.o. (20-fold the dose used in the previous pharmacological activity tests) does not alter rats motor coordination in the rotarod test, as shown in FIG. 5.

Figure 6:
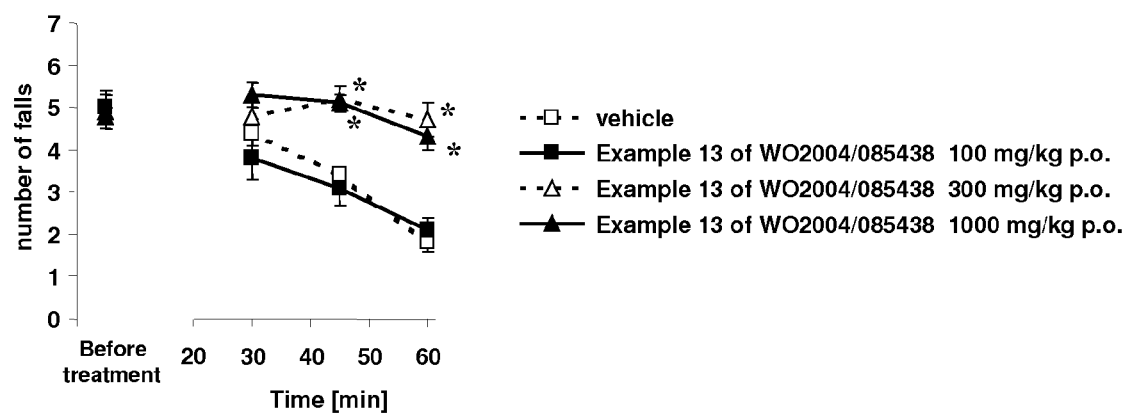
FIG. 6: Motor coordination in rats (rotarod)
Each value represents the mean±S.E.M. of the number of falls in 30 sec. of groups of 8 rats. *$p<0.01$ vs vehicle-treated animals.

Differently, as shown in FIG. 6, reference compound I-(3-cyanophenyl)-tetrahydropyrrolo[1,2-a]imidazole-2,5-dione (representative of compounds of formula (I) of WO2004/085438, see example 13) significantly altered animals motor coordination, increasing the number of falls starting from the dose of 300 mg/kg; these data show a lower tolerability level for the said reference compounds.

3.2 Rotarod/Ataxia Test in Rats

The $TD_{25}$ of dimiracetam was 6000 mg/kg p.o., thus demonstrating a very high safety and tolerability of the compound.

Among the reference standards, tramadol exhibited the highest toxicity, with a $TD_{50}$ of 253 mg/kg p.o., while pregabalin and levetiracetam showed $TD_{50}$s of 536 and 2000 mg/kg p.o. respectively. Gabapentin showed a $TD_{16}$ of 1000 mg/kg p.o.

3.3 Irwin Test in Rats

Dimiracetam administered at the dose of 1000 mg/kg by subcutaneous route and at the dose of 3000 mg/kg p.o. did not show any effects on all the behavioral parameters observed.

3.4 Hole Board Test in Mice

Figure 7:
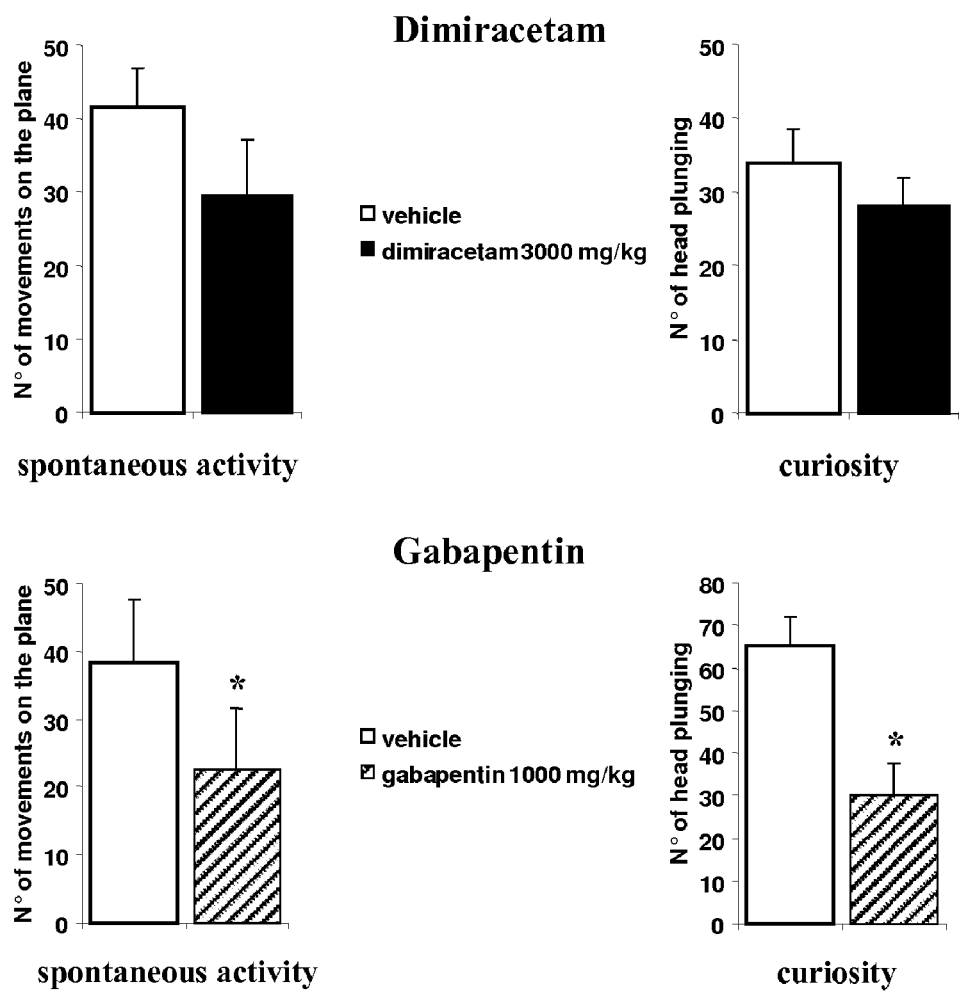
FIG. 7. Motor activity in mice (hole board)
*$p<0.01$ vs vehicle treated group. Each value represents the mean±S.E.M. of 18 mice. The test was performed 30 min after the oral administration of drugs.

In the hole board test, dimiracetam, administered at 3000 mg/kg p.o. does not significantly reduce either spontaneous activity (number of movements of each animal on the plane) or curiosity (number of head plungings), as shown in FIG. 7.

On the contrary, gabapentin administered at 1000 mg/kg causes a statistically significant reduction of both the evaluated parameters.

3.5 Preliminary Toxicity in Rats: Single Dose by Oral and Intravenous Route

Oral or intravenous administration of a single dose of 3000 mg/kg of dimiracetam to Sprague Dawley rats is substantially well tolerated. No signs of toxicity were observed during the experiment. Behavioral observation, blood and urine analyses did not show any dose-related variation of the measured clinical parameters.

3.6 Repeated Toxicity in Rats: 4 and 13 Weeks P.O.

Oral repeated administration of dimiracetam to Sprague Dawley rats, for 4 weeks and up to a maximal dose of 2500 mg/kg/day did not produce any changes in terms of mortality, symptomatology or changes of the normal behavior.

Oral repeated administration of dimiracetam to Sprague Dawley rats for 13 weeks and up to a maximal dose of 2500 mg/kg/day was well tolerated. No mortality or relevant clinical signs, as well as changes in terms of body weight, water and food consumption or in body temperature were seen at all dose levels. Hematology, clinical chemistry, coagulation parameters and urinalysis did not reveal drug related variation of the different parameters evaluated at all tested doses. No macro- or microscopic lesions or abnormalities correlated with the administration of dimiracetam were noticed.

3.7 Repeated Toxicity in Cynomolgus Monkeys: 4 and 13 Weeks P.O.

Oral repeated administration of dimiracetam in Cynomolgus monkeys for 4 weeks and up to a maximal dose of 2000 mg/kg/day, was well tolerated by the animals. A slight reduction in food consumption and body weight was observed in some animals treated with the maximal dose of 2000 mg/kg.

Oral repeated administration of dimiracetam in Cynomolgus monkeys for 13 weeks and up to a maximal dose of 2000 mg/kg/day was well tolerated by the animals. No mortality or relevant clinical signs, as well as changes in terms of body weight, water and food consumption or in body temperature were seen at all dose levels. Hematology, clinical chemistry, coagulation parameters and urinalysis did not reveal drug related variation of the different parameters evaluated at all tested doses. No macro- or microscopic lesions or abnormalities correlated with the administration of dimiracetam were noticed.

Taken together, these data show the insurgence of a strong antihyperalgesic activity for dimiracetam within the dosage ranges typical of the present invention. The high potency of action is confirmed by the fact that this compound showed remarkably higher efficacy than gabapentin, considered up to now the gold standard in chronic pain treatment therapy. Activity was found versus chronic pain of different origins (i.e. chemotherapy-induced pain, antiviral-induced pain, osteoarthritic pain, cephalea etc.) demonstrating the broad spectrum of applicability of the treatment proposed herein. In addition, data shown in said animal models highlight a special efficacy of dimiracetam versus chronic pain associated with antiviral treatment and osteoarthritic pain and related pathologies. In addition, at doses typical for the present invention, dimiracetam proved to be much more tolerable than gabapentin or pyrroloimidazole derivatives of prior art.

The invention claimed is:

1. A method for the treatment of pain induced by osteoarthritis, rheumatoid arthritis, wherein a pharmaceutically effective amount of dimiracetam, is administered to a subject in need thereof.

2. The method of claim 1 wherein the administration is performed either:
   orally in an amount of dimiracetam ranging from 10 to 300 mg/kg; or
   intramuscularly in an amount of dimiracetam ranging from 5 to 150 mg/kg; or
   intravenously in an amount of dimiracetam ranging from 2 to 60 mg/kg.

3. The method of claim 2, wherein the administration is performed via a dosage unit either:
   oral, wherein dimiracetam is present in amounts ranging from 500 to 15000 mg;
   intramuscular, wherein dimiracetam is present in amounts ranging from 250 to 7500 mg;
   intravenous, wherein dimiracetam is present in amounts ranging from 100 to 3000 mg.

4. The method of claim 1 for the treatment of pain induced by osteoarthritis.

5. The method of claim 1 for the treatment of pain induced by rheumatoid arthritis.

6. The method of claim 1 wherein the administration is performed
   orally in an amount of dimiracetam ranging from 10 to 300 mg/kg.

7. The method of claim 1 wherein the administration is performed
   intramuscularly in an amount of dimiracetam ranging from 5 to 150 mg/kg.

8. The method of claim 1 wherein the administration is performed
   intravenously in an amount of dimiracetam ranging from 2 to 60 mg/kg.

9. The method of claim 2, wherein the administration is performed via an oral dosage unit wherein dimiracetam is present in amounts ranging from 500 to 15000 mg.

10. The method of claim 2, wherein the administration is performed via an intramuscular dosage unit wherein dimiracetam is present in amounts ranging from 250 to 7500 mg.

11. The method of claim 2, wherein the administration is performed via an intravenous dosage unit wherein dimiracetam is present in amounts ranging from 100 to 3000 mg.

* * * * *